(12) United States Patent
Wu et al.

(10) Patent No.: US 10,935,498 B1
(45) Date of Patent: Mar. 2, 2021

(54) FLUORESCENT PROBE FOR DETECTING NITROREDUCTASE AND PREPARATION METHOD AND USE THEREOF IN ENZYMATIC REACTION

(71) Applicant: SOUTH CHINA UNIVERSITY OF TECHNOLOGY, Guangdong (CN)

(72) Inventors: Shuizhu Wu, Guangdong (CN); Lingfeng Xu, Guangdong (CN); Ling Ni, Guangdong (CN); Fang Zeng, Guangdong (CN)

(73) Assignee: SOUTH CHINA UNIVERSITY OF TECHNOLOGY, Guangdong (CN)

( * ) Notice: Subject to any disclaimer, the term of this patent is extended or adjusted under 35 U.S.C. 154(b) by 0 days.

(21) Appl. No.: 16/610,085

(22) PCT Filed: Mar. 26, 2019

(86) PCT No.: PCT/CN2019/079616
§ 371 (c)(1),
(2) Date: Nov. 1, 2019

(87) PCT Pub. No.: WO2020/107758
PCT Pub. Date: Jun. 4, 2020

(30) Foreign Application Priority Data

Nov. 30, 2018 (CN) .......................... 201811454833.X

(51) Int. Cl.
| | | |
|---|---|---|
| *C07D 215/14* | (2006.01) | |
| *G01N 21/76* | (2006.01) | |
| *C12Q 1/26* | (2006.01) | |
| *G01N 21/64* | (2006.01) | |
| *C09K 11/06* | (2006.01) | |

(52) U.S. Cl.
CPC ........... *G01N 21/76* (2013.01); *C07D 215/14* (2013.01); *C09K 11/06* (2013.01); *C12Q 1/26* (2013.01); *G01N 21/6428* (2013.01); *C09K 2211/1018* (2013.01); *G01N 2021/6432* (2013.01)

(58) Field of Classification Search
CPC .................................................. C07D 215/14
See application file for complete search history.

(56) References Cited

FOREIGN PATENT DOCUMENTS

| | | |
|---|---|---|
| CN | 105732564 | 7/2016 |
| CN | 107056618 | 8/2017 |
| CN | 108727223 | 11/2018 |
| CN | 105884734 | 12/2018 |
| CN | 109456264 | 3/2019 |
| WO | 2008030120 | 3/2008 |

OTHER PUBLICATIONS

"International Search Report (Form PCT/ISA/210) of PCT/CN2019/079616," dated Aug. 19, 2019, pp. 1-4.
Eiji Nakata, et al., "Design of a bioreductively-activated fluorescent pH probe for tumor hypoxia imaging," Bioorganic & Medicinal Chemistry, vol. 17, Aug. 2009, pp. 6952-6958.

*Primary Examiner* — Shawquia Jackson
(74) *Attorney, Agent, or Firm* — JCIPRNET

(57) ABSTRACT

The present invention relates to a fluorescent probe for detecting nitroreductase and a preparation method and use thereof in enzymatic reactions, belonging to the field of industrial analysis and detection. The fluorescent probe is 3-(4-(2-(4'-(diphenylamino)-3-((4-nitrobenzyl)oxy)-[1,1'-biphenyl]-4-yl)vinyl)quinolin-1-ium-1-yl)propane-1-sulfonate. The fluorescent probe of the present invention, with the introduction of hydrophilic groups, sulfonate and quinolinium, the probe's hydrophilicity is enhanced, under the enzymatic catalysis of nitroreductase (NTR), 1,6-rearrangement and elimination reaction occurs, and hydroxyl group is generated. Detection and analysis of the NTR in the industrial enzymatic reactions can be realized due to the change of fluorescence which is induced by the intramolecular charge transfer (ICT) effect. This method has such advantages as easy preparation, high yield and being suitable for detecting high concentration of enzyme in the enzymatic reactions, and it shows an extensive application prospect in the field of enzyme-detection in the industrial enzymatic reaction systems.

9 Claims, 6 Drawing Sheets

FLUORESCENT PROBE FOR DETECTING NITROREDUCTASE AND PREPARATION METHOD AND USE THEREOF IN ENZYMATIC REACTION

CROSS-REFERENCE TO RELATED APPLICATION

This application is a 371 of international application of PCT application serial no. PCT/CN2019/079616, filed on Mar. 26, 2019, which claims the priority benefit of China application no. 201811454833.X, filed on Nov. 30, 2018. The entirety of each of the above mentioned patent applications is hereby incorporated by reference herein and made a part of this specification.

BACKGROUND

Technical Field

The present invention relates to the technical field of industrial analysis and detection, and specifically relates to a fluorescent probe for detecting nitroreductase and a preparation method and use thereof in enzymatic reaction.

Description of Related Art

Nitro compounds are widely used in the fields of medicine, dyes, pesticides, explosives, and etc. However, owing to their carcinogenesis to human, most of the nitro compounds may cause many diseases and thus are harmful to human health. Amine compounds are essential to the synthesis of various fine chemical products and intermediates such as pesticides, medicine, dyes, synthetic resins, surfactants, and etc., for the introduction of amino group makes the change of function of the fine chemicals possible. For example, the introduction of amino group causes a red shift in the absorption and emission spectra of the compounds, the introduction of amino group to the ortho-position of a dye chromophore may result in a color change of the dye, and the introduction of amino group may alter the printing and dyeing property of the dye. More importantly, the amine compounds show less toxicity compared with the nitro compounds. At present, most of the aromatic amine compounds in the industry are prepared from the reduction of aromatic nitro compounds. Therefore, the reaction of reducing nitro group into amino group plays an important role in the industrial production.

Generally, the major reduction methods in the industry are as follows: reduction with iron powder, reduction with alkali sulfide, catalytic hydrogenation reduction and etc. However, these methods still have such drawbacks as complicated technological process, complex post-treatment, numerous wastes generated during the process, and high preparation cost. In recent years, biological method which can reduce the nitro compound into the amino compound is developing rapidly and it has become one of the methods that are environmentally-friendly and green-chemistry approaches. Enzyme, also called as ferment, being a kind of biocatalyst, is a biomacromolecule having biocatalytic function. Most of the enzymes are proteins, having relatively good biocompatibility and environmental friendliness. Enzymatic catalysis is regarded as a catalytic reaction between homogeneous phase catalytic reaction and heterogeneous phase catalytic reaction, which possesses not only characteristics of the general catalysts but also uniquenesses that differ from those of the general catalysts. Compared with the general catalysts, the enzymatic catalyst shows several advantages as follows: 1) an enzymatic reaction has high efficiency; 2) the enzymatic reaction has high specificity; 3) the enzymatic reaction is rather mild; 4) the diversity of the enzymes results in the diversity of the enzymatic reactions; 5) the performance of the enzymatic reaction can be adjusted by modulating the activity of the enzyme. However, since most of the enzymes are proteins, the activity of the enzyme may be affected by temperature, acidity or alkalinity, and concentration of the substrate, and even more the enzyme may be inactivated. Therefore, performing the enzymatic reaction in the aqueous media is preferable and conducive to reducing the environmental pollution caused by organic solvents and to facilitating the enzymatic reaction.

In recent years, with the improvement of the separation and purification technologies for enzymes, using a free enzyme to directly act on the reduction of nitro compounds has become a new field of the bio-organic chemistry. In particular, using oxidoreductases to reduce the nitro compounds has become a hot topic of research. The oxidoreductases that are mainly used for such kind of enzymatic reactions at present include nitroreductase and nitrate reductase. Particularly, nitroreductase is a kind of enzyme having a wide range of application and the source thereof is widely available. The conditions of the enzymatic reaction are mild, and the effect thereof is better. The research of the enzymatic reaction has been conducted more in-depth, and the reaction mechanism is relatively mature. In the meantime, there are two types of enzymes including the one sensitive to oxygen and the other one insensitive to oxygen, with wide range of applications. Thus, in order to guarantee the efficacy and stability of the enzymatic reactions that convert the nitro compounds into amine compounds in the industrial applications, it is of great significance to study and develop a fluorescent probe which is capable of measuring such kind of nitroreductase.

Fluorescence method has several excellent characteristics in analytic detection such as good selectivity, high sensitivity, quick response speed and ease of operation. Also, fluorescent compounds can fulfill the different needs of detecting various analytes, for they are easy to be designed, modified and improved in chemical structure. Therefore, the fluorescence method is particularly suitable for the analysis and detection of nitroreductase in the enzymatic reactions in industry. Chinese patent CN201610050741.X prepares a two-photon fluorescent probe for detecting nitroreductase in hypoxic region. The aromatic nitro in the compound can be reduced to an aromatic amino group by the nitroreductase, and the 1,6-rearrangement and elimination reaction occurs, releasing a fluorophore and resulting in a change of fluorescence. However, such fluorescent probe has poor water-solubility and exhibits aggregation-caused quenching of fluorescence. So, it is difficult to realize the detection and analysis of enzyme of high concentration and in an aqueous media. In the meantime, the two-photon detection instruments are rather complicated and expensive, the probe's application field mainly focuses on hypoxia in cells. Chinese patent CN201610471060.0 discloses a two-photon fluorescent probe for detecting nitroreductase, wherein the nitro group is directly coupled to the fluorophore, and with the increasing concentration of nitroreductase, the fluorescence intensity increases gradually with an emission wavelength ranging from 425 nm to 475 nm and from 500 nm to 550 nm. The probe is not suitable for use in the aqueous media, and fluorescence quenching would easily occur when a high concentration of nitroreductase is present. This probe is mainly used in the biological field such as cell imaging, without application potential for industrial enzymatic reaction in large scale.

When a fluorescent material with aggregation-induced emission (AIE) feature exists in the form of monomolecularly dissolved state in solution, electrons in the excited state return to the ground state through the intramolecular motions; when the molecules are in the aggregation state, the intramolecular motions are restricted and the electrons in the excited state may return to the ground state only through the radiative pathway, and thus enhanced fluorescence can be observed which has extensive applications in many fields. Chinese patent CN201710009923.7 discloses a fluorescent probe based on AIE feature for detecting nitroreductase, wherein a nitro group is directly coupled to tetraphenylethylene. Before response to nitroreductase, it shows strong fluorescence due to the D-π-A electronic effect; and after the response, the fluorescence becomes faint and blue shift occurs due to the D-π-D structure. The detection of nitroreductase is realized by using such change of fluorescence. However, the probe is mainly used in the cells and unable to be applied in the detection and analysis of the concentration of enzyme in the industrial enzymatic reaction systems.

Although there's already some progress of the fluorescent probes for detecting nitroreductase in the field of biological detection and imaging, it is still rare to apply the fluorescent probes to detection and analysis of the enzymatic activity in the industrial enzymatic reactions. It is clear that, there's urgent need of developing a probe with specific catalysis effect for detecting and analyzing enzymatic activity for the field of industrial enzymatic reactions.

SUMMARY

In order to solve the drawbacks and deficiencies in the prior art, the primary objective of the present invention is to provide a fluorescent probe compound. The fluorescent probe has aggregation-induced emission feature. With the introduction of hydrophilic groups, sulfonate and quinolinium, the hydrophilicity of the probe is enhanced, a 1,6-rearrangement and elimination reaction occurs under the catalysis of a nitroreductase (NTR), and a hydroxyl group is generated. Detection and analysis of NTR in the industrial enzymatic reactions can be realized due to the change of fluorescence which is induced by the intramolecular charge transfer (ICT) effect.

Another objective of the present invention is to provide a preparation method of the fluorescent compound.

Another objective of the present invention is to provide use of the fluorescent compound for detecting activity of the nitroreductase in the industrial enzymatic reactions for converting aromatic nitro into aromatic amino.

The objectives of the present invention are realized by the following technical solutions.

A fluorescent probe for detecting nitroreductase, wherein the fluorescent probe is 3-(4-(2(4'-(diphenylamino)-3-((4-nitrobenzyl)oxy)-[1,1'-biphenyl]-4-yl)vinyl)quinolin-1-ium-1-yl)propane-1-sulfonate, having a structural formula as follows:

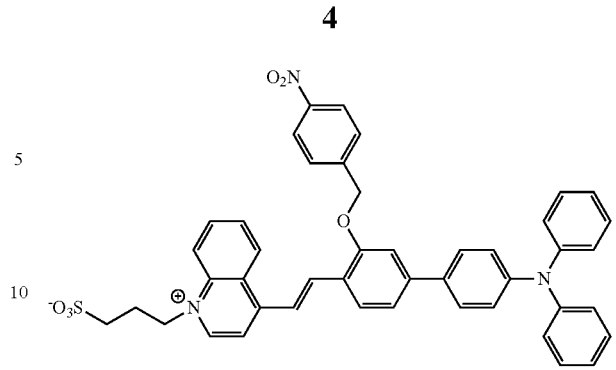

A preparation method of the above fluorescent probe for detecting nitroreductase, includes the following steps:

(1) dissolving 4'-(diphenylamino)-3-hydroxy-[1,1'-biphenyl]-4-carbaldehyde into dimethyl sulfoxide to obtain a solution 1, dissolving 1-(bromomethyl)-4-nitrobenzene into tetrahydrofuran to obtain a solution 2, subjecting the solution 1 and the solution 2 to ultrasonic treatment respectively and then mixing together, adding cesium carbonate to perform a reaction, controlling a reaction temperature in the range of 50° C.-150° C., separating and purifying a reaction product to obtain 4'-(diphenylamino)-3-((4-nitrobenzyl)oxy)-[1,1'-biphenyl]-4-carbaldehyde in yellow solid powder;

(2) dissolving 3-(4-methylquinolin-1-ium-1-yl)propane-1-sulfonate into pyridine, then adding acetic acid, followed by sufficient mixing, then adding 4'-(diphenylamino)-3-((4-nitrobenzyl)oxy)-[1,1'-biphenyl]-4-carbaldehyde obtained in step (1), heating to 25° C.-80° C. with stirring to perform reaction, separating and purifying a reaction product to obtain 3-(4-(2-(4'-(diphenylamino)-3-((4-nitrobenzyl)oxy)-[1,1'-biphenyl]-4-yl)vinyl)quinolin-1-ium-1-yl)propane-1-sulfonate in purplish-red solid powder.

Preferably, a molar ratio of dosages of 4'-(diphenylamino)-3-hydroxy-[1,1'-biphenyl]-4-carbaldehyde to 1-(bromomethyl)-4-nitrobenzene in step (1) is 1:(1.5-2).

Preferably, a molar ratio of dosages of cesium carbonate to 1-(bromomethyl)-4-nitrobenzene in step (1) is (4-5):1.

Preferably, a molar ratio of dosages of 3-(4-methylquinolin-1-ium-1-yl)propane-1-sulfonate to 4'-(diphenylamino)-3-((4-nitrobenzyl)oxy)-[1,1'-biphenyl]-4-carbaldehyde in step (2) is 1:(1-2).

Preferably, a molar ratio of dosages of acetic acid to 3-(4-methylquinolin-1-ium-1-yl)propane-1-sulfonate in step (2) is (2-4):1.

Preferably, the reaction in step (1) lasts for 5 hours to 48 hours.

Preferably, the reaction in step (2) lasts for 3 hours to 24 hours.

Preferably, the separating and purifying in step (1) are as follows: cooling a reaction mixture to room temperature, extracting the reaction mixture with dichloromethane/deionized water, collecting an organic phase followed by drying and filtering, removing a solvent by rotary evaporation, and purifying the obtained solid via a silica gel chromatographic column.

Preferably, the separating and purifying in step (2) are as follows: cooling a reaction mixture to room temperature, removing a solvent by rotary evaporation, then adding ethyl acetate and washing with hydrochloric acid and saturated salt solution respectively, followed by drying and filtering, removing a solvent by rotary evaporation, and purifying the obtained solid via a silica gel chromatographic column.

Use of the fluorescent probe for detecting nitroreductase in detecting and analyzing the nitroreductase in an enzymatic reaction of converting aromatic nitro into aromatic amino in the industry.

The fluorescent compound, the product obtained in the present invention, is 3-(4-(2-(4'-(diphenylamino)-3-((4-nitrobenzyl)oxy)-[1,1'-biphenyl]-4-yl)vinyl)quinolin-1-ium-1-yl)propane-1-sulfonate (TAE-NQS), with a molecular formula of C45H37N3O6S and a relative molecular weight of 747.24. Being purplish-red and odourless solid powder, the TAE-NQS is slightly soluble in water and easily soluble in solvents such as DMSO and DMF. Having good photostability and being non-toxic, the compound is suitable for being used in enzymatic reactions in aqueous media. Since the TAE-NQS has a triphenylamine group, and the fluorescence is significantly quenched due to the nitro group on the recognition moiety, there's hardly fluorescence emission near 750 nm under the excitation of 500 nm. When the TAE-NQS reacts with the nitroreductase, a 1,6-rearrangement and elimination reaction occurs, and hydroxyl group is generated through cleavage reaction (the response product is 3-(4-(2-(4'-(diphenylamino)-3-((4-nitrobenzyl)oxy)-[1,1'-biphenyl]-4-yl)vinyl)quinolin-1-ium-1-yl)propane-1-sulfonate, TAE-NQS-OH). Meanwhile, the response product also has the aggregation-induced emission feature due to the existence of the AIE-active triphenylamine group. The fluorescent probe of the present invention can be used for detecting the activity of nitroreductase in the industrial enzymatic reactions for converting aromatic nitro into aromatic amino. The recognition mechanism is shown as follows:

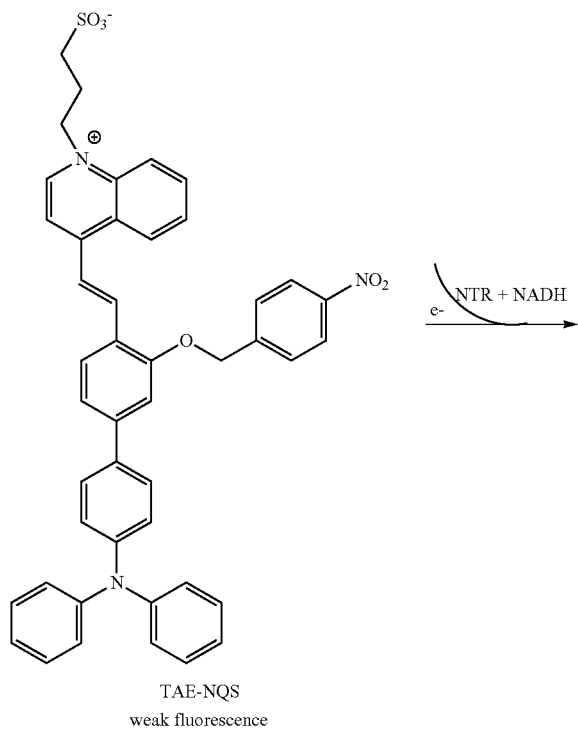

TAE-NQS
weak fluorescence

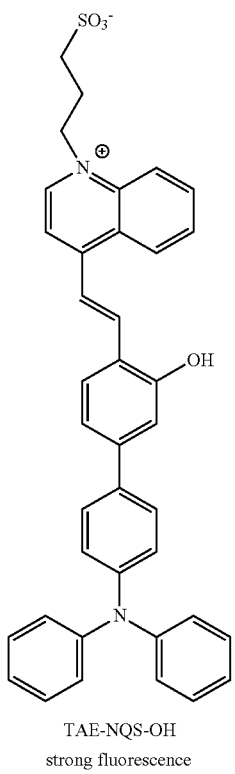

TAE-NQS-OH
strong fluorescence

The present invention provides a fluorescent probe for detecting the nitroreductase in the reactions of converting phenyl nitro into phenyl amino in the industrial enzymatic reactions. The probe has merely weak fluorescence, but with the enzymatic reaction by nitroreductase, the phenyl nitro is reduced into phenyl amino, and the 1,6-rearrangement and elimination reaction occurs to generate the hydroxyl group through cleavage reaction resulting in strong fluorescence.

Compared with the prior art, the present invention has the following advantages and beneficial effects:

(1) The fluorescent compound, TAE-NQS, of the present invention has aggregation-induced emission feature. In most cases, in order to improve the reaction efficiency of the enzymatic reaction in the field of chemical industry, high concentration of enzyme would usually be added to the reaction system. Whereas with the existence of high concentration of substrate, the present probe will not be quenched, and the detecting effect with good sensitivity and accuracy can be obtained.

(2) After the enzymatic catalysis reaction by nitroreductase, 1,6-rearrangement and elimination reaction occurs in the probe TAE-NQS of the present invention. After the cleavage reaction, the intramolecular "mechanical rotations" and also the non-radiative energy dissipation pathway from the excited state to the ground state are restricted because of the existence of triphenylamine, hence the probe still has aggregation-induced emission feature. Meanwhile, hydroxyl group is generated so that the fluorescence changes. Therefore, the probe TAE-NQS can be used in the detection and analysis of nitroreductase in the industrial enzymatic reactions, especially the reactions of converting aromatic nitro into aromatic amino.

(3) The fluorescent probe of the present invention has relatively long emission wavelength reaching up to 750 nm, and has significant fluorescence-enhancement effect.

(4) The fluorescent probe of the present invention is suitable for relatively harsh and complicated environment in the industrial enzymatic reactions, having good structural stability and being easy to be promoted and applied in the enzymatic reactions in chemical industry.

DESCRIPTION OF THE EMBODIMENTS

The present invention is further described in detail with the examples and accompanied drawings, and implementation of the present invention is not limited to these.

Figure 1:
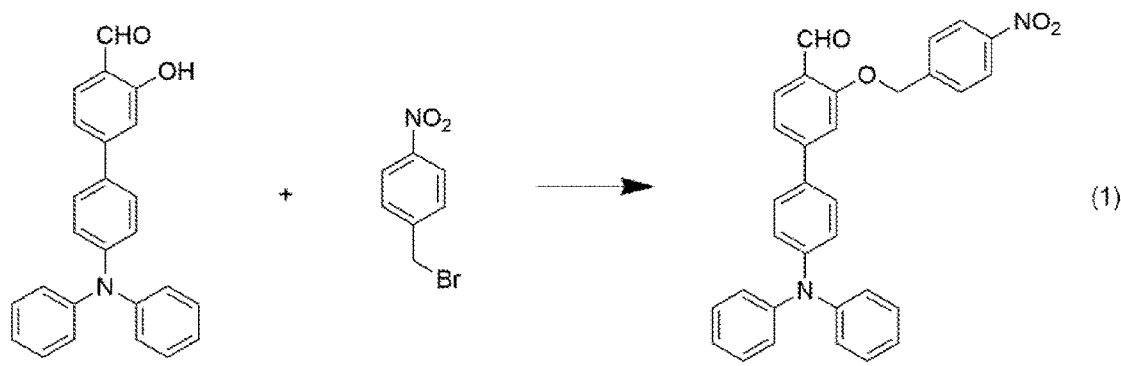
FIG. 1 shows a synthetic route of a fluorescent probe compound of the present invention.
Figure 1:
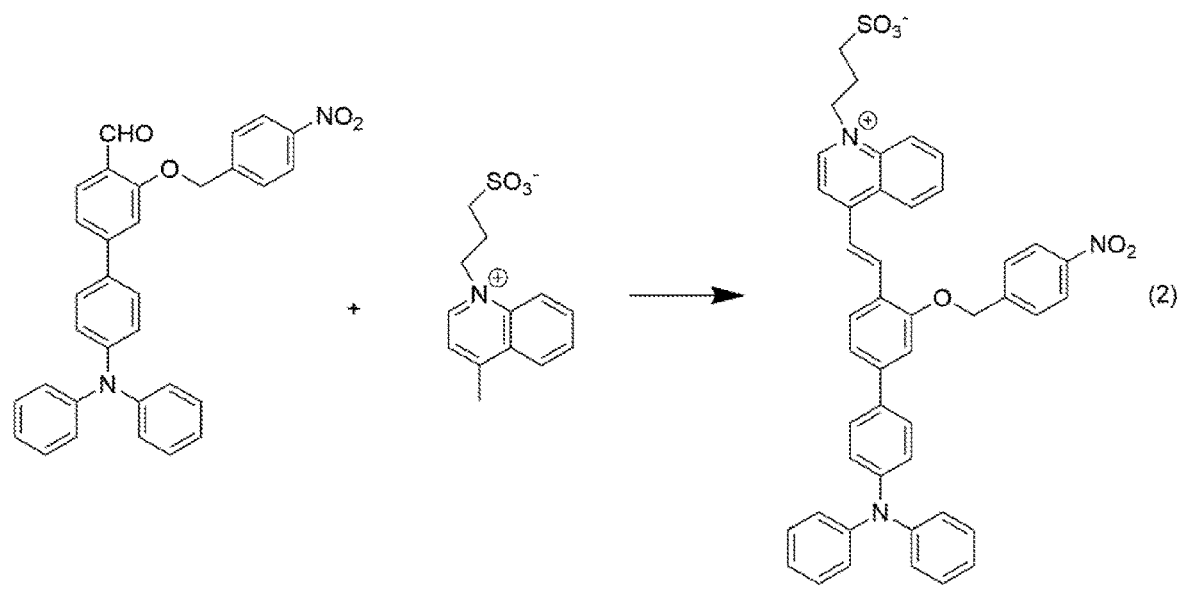

A synthetic route of a fluorescent probe compound of the present invention is shown as FIG. 1.

Example 1

Figure 2:
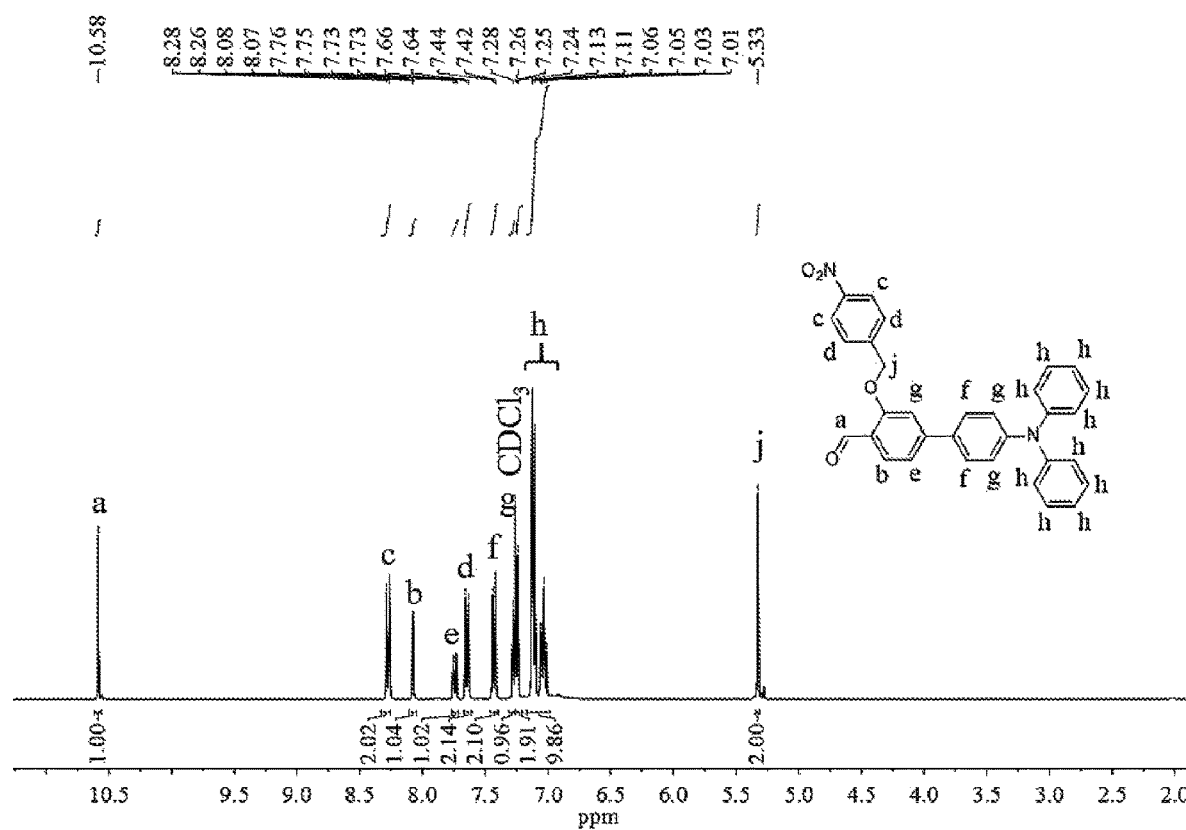
FIG. 2 shows a $^1$H-NMR spectrum of 4'-(diphenylamino)-3-((4-nitrobenzyl)oxy)-[1,1'-biphenyl]-4-carbaldehyde in Example 1.

(1) 365 mg of 4'-(diphenylamino)-3-hydroxy-[1,1'-biphenyl]-4-carbaldehyde was dissolved in 10 mL of dimethyl sulfoxide, 324 mg of 1-(bromomethyl)-4-nitrobenzene was dissolved in 10 mL of tetrahydrofuran, followed by ultrasonic treatment respectively, and then they were mixed together. 1.96 g of cesium carbonate was added to perform a reaction of which a reaction temperature was maintained at 50° C. and which lasted for 5 hours. An obtained reaction mixture was cooled to room temperature and extracted with dichloromethane/deionized water, an organic phase was collected, dried and filtered, the solvent was removed by rotary evaporation, and an obtained solid was purified via a silica gel chromatographic column (an eluent used is dichloromethane/petroleum ether, V/V=2:1). A product, 405 mg of 4'-(diphenylamino)-3-((4-nitrobenzyl)oxy)-[1,1'-biphenyl]-4-carbaldehyde in yellow solid powder, was obtained (with a yield of 81%). The product was characterized by $^1$H-NMR, wherein $^1$H NMR (400 MHz, CDCl$_3$) δ (TMS, ppm): 10.58 (s, 1H), 8.27 (d, J=8.6 Hz, 2H), 8.07 (d, J=2.4 Hz, 1H), 7.74 (dd, J=8.6, 2.4 Hz, 1H), 7.65 (d, J=8.5 Hz, 2H), 7.43 (d, J=8.6 Hz, 2H), 7.28 (s, 1H), 7.24 (d, J=10.8, 4.8 Hz, 2H), 7.12 (d, J=8.3 Hz, 6H), 7.04 (dd, J=12.8, 5.6 Hz, 4H), 5.33 (s, 2H). Specifically, the proton peak at 10.58 ppm is the proton peak of the aldehyde group in the structure of salicylaldehyde, the proton peaks at 8.02 ppm, 7.75 ppm and 7.28 ppm are proton peaks of three hydrogen atoms in the aromatic ring of salicylaldehyde, the proton peaks at 8.26 ppm and 7.66 ppm are proton peaks of four hydrogen atoms in 1-(bromomethyl)-4-nitrobenzene, the characteristic peaks of four protons on one of the aromatic rings of triphenylamine are near 7.40 ppm and 7.27 ppm, the characteristic peaks of the rest 10 protons on the aromatic rings of triphenylamine lie at 7.0 ppm-7.24 ppm, and the proton peaks at 5.33 ppm are the characteristic peaks of methylene in 1-(bromomethyl)-4-nitrobenzene. It can be determined through the analysis of $^1$H-NMR spectrum that the product synthesized is the target intermediate. The $^1$H-NMR spectrum of the obtained product is shown as FIG. 2.

Figure 3:
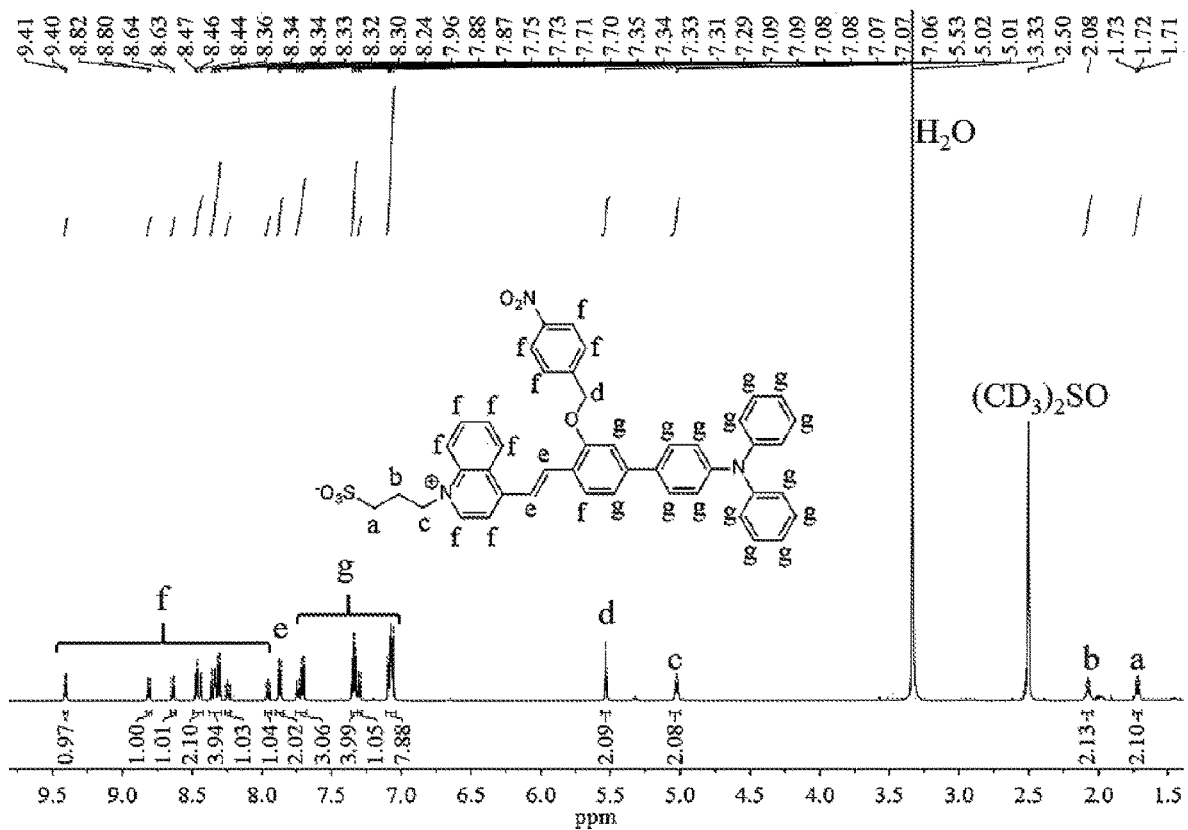
FIG. 3 shows a 1H-NMR spectrum of 3-(4-(2-(4'-(diphenylamino)-3-((4-nitrobenzyl)oxy)-[1,1'-biphenyl]-4-yl)vinyl)quinolin-1-ium-1-yl)propane-1-sulfonate in Example 1.

(2) 265 mg of 3-(4-methylquinolin-1-ium-1-yl)propane-1-sulfonate was dissolved in 10 mL of pyridine, and 114 μL of acetic acid was added, followed by sufficient mixing. Then, 500 mg of 4'-(diphenylamino)-3-((4-nitrobenzyl)oxy)-[1,1'-biphenyl]-4-carbaldehyde was added, heated to 25° C. with stirring to perform a reaction which lasted for 3 hours. An obtained reaction mixture was cooled to room temperature and subjected to rotary evaporation to remove the solvent, and then excessive ethyl acetate was added. The mixture was washed with hydrochloric acid for 3 times and salt solution for 1 time respectively, dried with anhydrous sodium sulfate, and subjected to suction filtration and rotary evaporation to remove solvent. An obtained solid was purified via a silica gel chromatographic column (an eluent used is dichloromethane/methanol, V/V=5:1). 448 mg of 3-(4-(2-(4'-(diphenylamino)-3-((4-nitrobenzyl)oxy)-[1,1'-biphenyl]-4-yl)vinyl)quinolin-1-ium-1-yl)propane-1-sulfonate in purplish-red solid powder was obtained (with a yield of 60%). The product was characterized by 1H-NMR, wherein 1H NMR (600 MHz, DMSO) δ (TMS, ppm): 9.41 (d, J=6.5 Hz, 1H), 8.81 (d, J=8.2 Hz, 1H), 8.64 (d, J=9.0 Hz, 1H), 8.46 (t, J=11.2 Hz, 2H), 8.37-8.29 (m, 4H), 8.27-8.22 (m, 1H), 7.98-7.94 (m, 1H), 7.87 (d, J=8.7 Hz, 2H), 7.72 (dd, J=20.4, 9.8 Hz, 3H), 7.37-7.31 (m, 4H), 7.30 (d, J=8.8 Hz, 1H), 7.11-7.04 (m, 8H), 5.53 (s, 2H), 5.02 (t, J=7.5 Hz, 2H), 2.12-2.05 (m, 2H), 1.76-1.69 (m, 2H). Specifically, the proton peaks at positions a, b and c are the characteristic peaks of three methylene protons on the alkylsulfonate respectively, the proton peaks at position d are the characteristic peaks of the methylene protons in 1-(bromomethyl)-4-nitrobenzene, the proton peaks at position e are the characteristic peaks of the protons on the conjugated double bond structure, the protons at position g are the characteristic peaks of 16 hydrogen protons on the triphenylamine and the aromatic ring of salicylaldehyde coupled thereto, the proton peaks of the quinolinium and the aromatic ring of 1-(bromomethyl)-4-nitrobenzene and those near the double bond of salicylaldehyde lie at 7.78 ppm-9.5 ppm, and there are 11 characteristic peaks of hydrogen protons in total. It can be determined through the analysis on 1H-NMR spectrum that the product synthesized is the target product. The 1H-NMR spectrum of the obtained product is shown as FIG. 3.

Example 2

(1) 365 mg of 4'-(diphenylamino)-3-hydroxy-[1,1'-biphenyl]-4-carbaldehyde was dissolved in 10 mL of dimethyl sulfoxide, 389 mg of was dissolved in 10 mL of tetrahydrofuran, followed by ultrasonic treatment respectively, and then they were mixed together. 2.64 g of cesium carbonate was added to perform a reaction of which a reaction temperature was maintained at 100° C. and which lasted for 24 hours. An obtained reaction mixture was cooled to room temperature and extracted with dichloromethane/deionized water, an organic phase was collected, dried and filtered, the solvent was removed by rotary evaporation, and an obtained solid was purified via a silica gel chromatographic column (an eluent used is dichloromethane/petroleum ether, V/V=2:1). A product, 415 mg of 4'-(diphenylamino)-3-((4-nitrobenzyl)oxy)-[1,1'-biphenyl]-4-carbaldehyde in yellow solid powder, was obtained (with a yield of 83%).

(2) 265 mg of 3-(4-methylquinolin-1-ium-1-yl)propane-1-sulfonate was dissolved in 10 mL of pyridine, and 171 µL of acetic acid was added, followed by sufficient mixing. Then, 750 mg of 4'-(diphenylamino)-3-((4-nitrobenzyl)oxy)-[1,1'-biphenyl]-4-carbaldehyde was added, heated to 50° C. with stirring to perform a reaction which lasted for 12 hours. An obtained reaction mixture was cooled to room temperature and subjected to rotary evaporation to remove the solvent, and then excessive ethyl acetate was added. The mixture was washed with hydrochloric acid for 3 times and salt solution for 1 time respectively, dried with anhydrous sodium sulfate, and subjected to suction filtration and rotary evaporation to remove the solvent. An obtained solid was purified via a silica gel chromatographic column (an eluent used is dichloromethane/methanol, V/V=5:1). 485 mg of 3-(4-(2-(4'-(diphenylamino)-3-((4-nitrobenzyl)oxy)-[1,1'-biphenyl]-4-yl)vinyl)quinolin-1-ium-1-yl)propane-1-sulfonate in purplish-red solid powder was obtained (with a yield of 65%).

The characterization results for the obtained intermediate compound and the fluorescent probe compound TAE-NQS in the present example are the same as those in Example 1.

Example 3

(1) 365 mg of 4'-(diphenylamino)-3-hydroxy-[1,1'-biphenyl]-4-carbaldehyde was dissolved in 10 mL of dimethyl sulfoxide, 432 mg of 1-(bromomethyl)-4-nitrobenzene was dissolved in 10 mL of tetrahydrofuran, followed by ultrasonic treatment respectively, and then they were mixed together. 3.26 g of cesium carbonate was added to perform a reaction of which a reaction temperature was maintained at 150° C. and which lasted for 48 hours. An obtained reaction mixture was cooled to room temperature and extracted with dichloromethane/deionized water, an organic phase was collected, dried and filtered, solvent was removed by rotary evaporation, and an obtained solid was purified via a silica gel chromatographic column (an eluent used is dichloromethane/petroleum ether, V/V=2:1). A product, 430 mg of 4'-(diphenylamino)-3-((4-nitrobenzyl)oxy)-[1,1'-biphenyl]-4-carbaldehyde in yellow solid powder, was obtained (with a yield of 86%).

(2) 265 mg of 3-(4-methylquinolin-1-ium-1-yl)propane-1-sulfonate was dissolved in 10 mL of pyridine, and 228 µL of acetic acid was added, followed by sufficient mixing. Then, 1000 mg of 4'-(diphenylamino)-3-((4-nitrobenzyl)oxy)-[1,1'-biphenyl]-4-carbaldehyde was added, heated to 80° C. with stirring to perform a reaction which lasted for 24 hours. An obtained reaction mixture was cooled to room temperature and subjected to rotary evaporation to remove solvent, and then excessive ethyl acetate was added. The mixture was washed with hydrochloric acid for 3 times and salt solution for 1 time respectively, dried with anhydrous sodium sulfate, and subjected to suction filtration and rotary evaporation to remove solvent. An obtained solid was purified via a silica gel chromatographic column (an eluent used is dichloromethane/methanol, V/V=5:1). 470 mg of 3-(4-(2-(4'-(diphenylamino)-3-((4-nitrobenzyl)oxy)-[1,1'-biphenyl]-4-yl)vinyl)quinolin-1-ium-1-yl)propane-1-sulfonate in purplish-red solid powder was obtained (with a yield of 63%).

The characterization results for the obtained intermediate compound and the fluorescent probe compound TAE-NQS in the present example are the same as those in Example 1.

Tests of the obtained fluorescent probe compound of the present invention used to detect activity of nitroreductase in an enzymatic reaction system:

1.5 mg of the solid fluorescent compound, 3-(4-(2-(4'-(diphenylamino)-3-((4-nitrobenzyl)oxy)-[1,1'-biphenyl]-4-yl)vinyl)quinolin-1-ium-1-yl)propane-1-sulfonate (TAE-NQS, prepared in Example 1), was dissolved in 2 mL of DMSO, and prepared into a 1 mM stock solution of the fluorescent compound. Before the test, of the fluorescent compound was diluted with a phosphate buffer (10 mM, pH 7.4), and a solution system to be tested containing 1% DMSO was obtained (final concentration of the probe was 10 µM).

Figure 4:
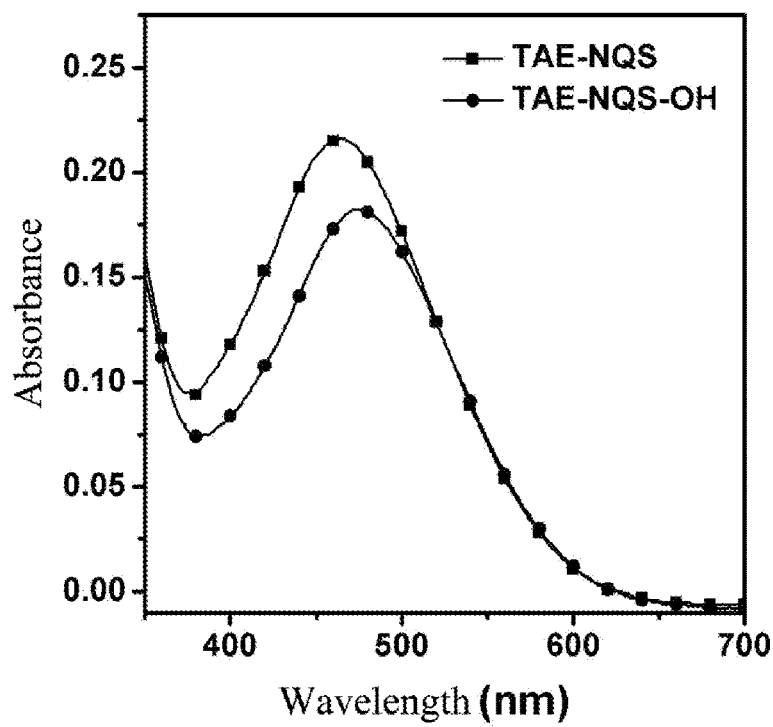
FIG. 4 shows absorption spectra of the fluorescent probe of the present invention before and after response.
Figure 5:
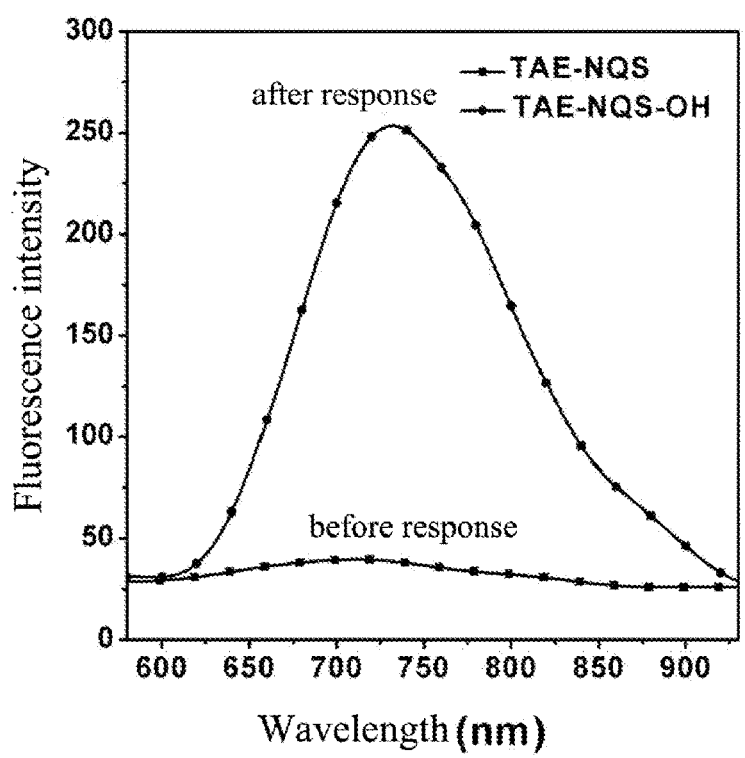
FIG. 5 shows fluorescence spectra of the fluorescent probe of the present invention before and after response.
Figure 6:
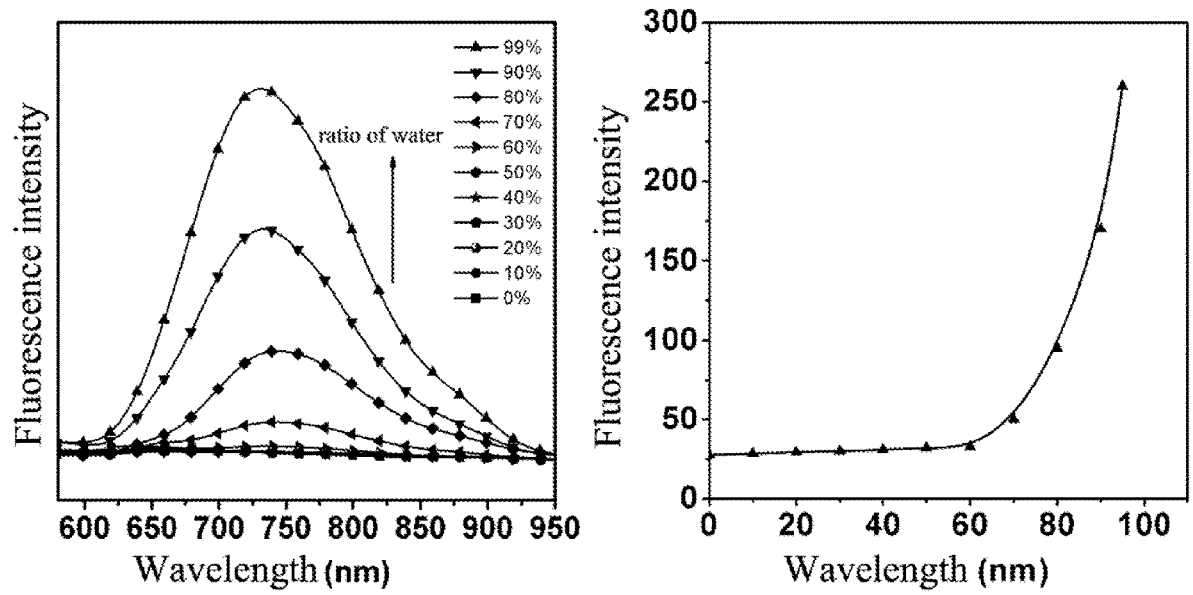
FIG. 6 shows fluorescence spectra displaying the aggregation-induced emission feature of the response product TAE-NQS-OH.

(1) Fluorescence property of the probe compound TAE-NQS:

3 µL of the above-mentioned stock solution of the fluorescent compound was drawn, and a blank control sample and test samples were prepared with PBS buffer solution (10 mM, pH=7.4). The concentration of the probe compound in the blank sample was 10 µM, without adding nitroreductase and coenzyme substance (reduced form of nicotinamide adenine dinucleotide (NADH), as the control sample. The concentration of the probe compound in the test samples was controlled to 10 µM, and the final concentration of nitroreductase was controlled to 2 µg/mL, and the concentration of the coenzyme substance NADH was controlled to 100 µM. The samples were incubated at 37° C. for 15 minutes, then the absorption spectra ranging from 350 nm to 700 nm were recorded, and the fluorescence spectra were measured under the excitation light of 500 nm. The results are shown as FIG. 4 and FIG. 5. Compared with the blank sample, red shift in the absorption of the test samples occurred and the fluorescence intensity changed significantly. This is because when the NTR was present, 1,6-rearrangement and elimination reaction occurred in the probe molecules in the test samples, after the cleavage reaction, the generated hydroxyl group was an electron-donating group, and then 3-(4-(2-(4'-(diphenylamino)-3-((4-nitrobenzyl)oxy)-[1,1'-biphenyl]-4-yl)vinyl)quinolin-1-ium-1-yl)propane-1-sulfonate (TAE-NQS-OH, the response product) was formed, resulting in the intramolecular charge transfer effect (ICT effect) and thus a red shift in the fluorescence. Meanwhile, the fluorescent molecule has a relatively good AIE effect due to the existence of triphenylamine—the AIE group. The test results of the AIE effect of TAE-NQS-OH are shown as FIG. 6 (by adjusting a ratio of water to N,N-dimethylformamide to be 0%-99% and controlling the concentration in each test solution to be 10 µM, the test solutions for the aggregation-induced emission feature were prepared).

Figure 7:
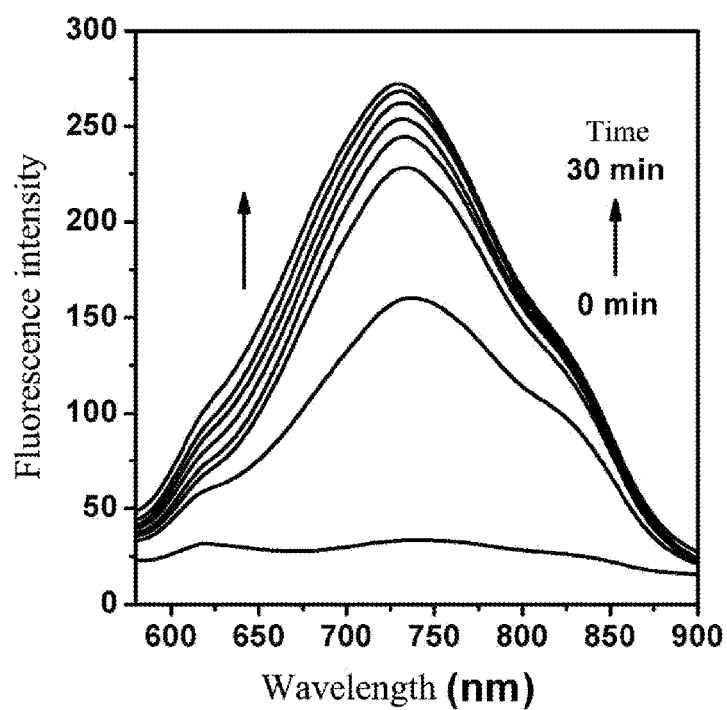
FIG. 7 shows fluorescence spectra of the fluorescent probe TAE-NQS in response to nitroreductase for different time.
Figure 8:
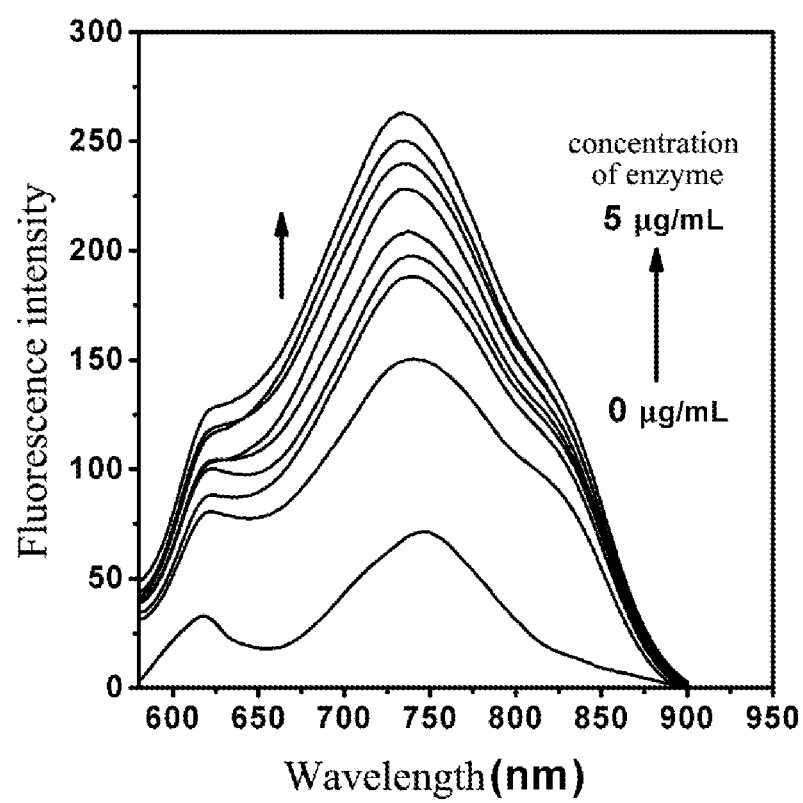
FIG. 8 shows fluorescence spectra of the fluorescent probe TAE-NQS in response to different concentrations of nitroreductase.

(2) Fluorescent response test of the probe compound TAE-NQS to different concentrations of NTR in PBS buffer, and response time test:

When the concentration of NTR was 2 µg/mL and the concentration of the probe was 10 µM, the fluorescence intensity varied over time, shown as FIG. 7. Additionally, a series of PBS buffer solutions (pH=7.4) with the concentration of the probe being 10 µM and the concentration of NTR being 0, 0.25, 0.5, 0.75, 1, 1.5, 2, 3, 5 µg/mL respectively, were prepared. By controlling the temperature to be 37° C. and the incubation time to be 5 minutes, the fluorescence spectra under the excitation wavelength of 500 nm for each test sample were recorded. The test results were shown as FIG. 8. It can be seen from FIG. 7 and FIG. 8 that the fluorescent probe prepared by the present invention has relatively good detecting effect on the NTR in the enzymatic reaction system. With the increasing concentration of NTR (0 μg/mL to 5 μg/mL), the enzymatic reaction was completed within 30 minutes, and the fluorescence changed significantly after the response. It demonstrates that the probe is suitable for being used in detecting the nitroreductase in reactions of converting aromatic nitro into aromatic amino.

This method has advantages including easy preparation, high yield and being suitable for detecting high concentration of enzyme in the enzymatic reactions, and it shows an extensive application prospect in the field of enzyme-detection in the industrial enzymatic reaction systems.

The above examples are preferable implementations of the present invention, and the implementations of the present invention are not limited to the above examples. Any other variation, modification, substitution, combination and simplification that are made without departing from the spirit and scope of the present invention are intended to be equivalents, and should be included in the scope of protection of the present invention.

What is claimed is:

1. A fluorescent probe for detecting nitroreductase, wherein the fluorescent probe is 3-(4-(2-(4'-(diphenylamino)-3-((4-nitrobenzyl)oxyl)-[1,1'-biphenyl]-4-yl)vinyl)quinoline-1-bromine)propane-1-sulfonate, having a structural formula as follows:

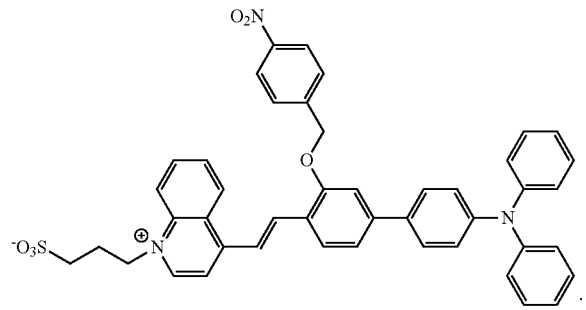

2. A preparation method of the fluorescent probe for detecting nitroreductase according to claim 1, wherein comprising the following steps:
   (1) dissolving 4'-(diphenylamino)-3-hydroxy-[1,1'-biphenyl]-4-carbaldehyde into dimethyl sulfoxide and dissolving 1-(bromomethyl)-4-nitrobenzene into tetrahydrofuran, followed by ultrasonic treatment respectively and then mixing together, adding cesium carbonate, controlling a reaction temperature in the range of 50° C.-150° C., separating and purifying a reaction product to obtain 4'-(diphenylamino)-3-((4-nitrobenzyl)oxy)-[1,1'-biphenyl]-4-carbaldehyde in yellow solid powder;
   (2) dissolving 3-(4-methylquinoline-1-bromine)propane-1-sulfonate into pyridine, then adding acetic acid, followed by sufficient mixing, then adding the 4'-(diphenylamino)-3-((4-nitrobenzyl)oxy)-[1,1'-biphenyl]-4-carbaldehyde obtained in step (1), heating to 25° C.-80° C. with stirring to perform reaction, separating and purifying a reaction product to obtain 3-(4-(2-(4'-(diphenylamino)-3-((4-nitrobenzyl)oxyl)-[1,1'-biphenyl]-4-yl)vinyl)quinoline-1-bromine)propane-1-sulfonate in purplish-red solid powder.

3. The preparation method according to claim 2, wherein a molar ratio of dosages of 4'-(diphenylamino)-3-hydroxy-[1,1'-biphenyl]-4-carbaldehyde to 1-(bromomethyl)-4-nitrobenzene in step (1) is 1:1.5-2.

4. The preparation method according to claim 2, wherein a molar ratio of dosages of cesium carbonate to 1-(bromomethyl)-4-nitrobenzene in step (1) is 4-5:1.

5. The preparation method according to claim 2, wherein a molar ratio of dosages of 3-(4-methylquinoline-1-bromine)propane-1-sulfonate to 4'-(diphenylamino)-3-((4-nitrobenzyl)oxy)-[1,1'-biphenyl]-4-carbaldehyde in step (2) is 1:1-2.

6. The preparation method according to claim 2, wherein a molar ratio of dosages of acetic acid to 3-(4-methylquinoline-1-bromine)propane-1-sulfonate in step (2) is 2-4:1.

7. The preparation method according to claim 2, wherein the reaction in step (1) lasts for 5 hours to 48 hours.

8. The preparation method according to claim 2, wherein the reaction in step (2) lasts for 3 hours to 24 hours.

9. The preparation method according to claim 2, wherein the separating and purifying in step (1) are as follows: cooling a reaction mixture to room temperature, extracting with dichloromethane/deionized water, collecting an organic phase followed by drying and filtering, removing a solvent by rotary evaporation, and purifying the obtained solid via a silica gel chromatographic column; and wherein the separating and purifying in step (2) are as follows: cooling a reaction mixture to room temperature, removing a solvent by rotary evaporation, then adding ethyl acetate and washing with hydrochloric acid and saturated salt solution respectively, followed by drying and filtering, removing a solvent by rotary evaporation, and purifying the obtained solid via a silica gel chromatographic column.

* * * * *